United States Patent
Benz et al.

(10) Patent No.: US 6,732,917 B1
(45) Date of Patent: May 11, 2004

(54) APPARATUS FOR AUTOMATIC MEASUREMENT OF MEASURING FIELDS

(75) Inventors: Christian Benz, Unterehrendingen (CH); Thomas Senn, Dielsdorf (CH)

(73) Assignee: Gretag-Macbeth AG, Regensdorf (CH)

( * ) Notice: Subject to any disclaimer, the term of this patent is extended or adjusted under 35 U.S.C. 154(b) by 0 days.

(21) Appl. No.: 09/680,206

(22) Filed: Oct. 6, 2000

(30) Foreign Application Priority Data

Oct. 11, 1999 (EP) .............................. 99119939

(51) Int. Cl.⁷ .............................. G06F 17/60
(52) U.S. Cl. .................. 235/379; 250/226; 356/73; 356/406; 436/46
(58) Field of Search ................ 250/226; 235/379; 356/73, 406; 436/46; 358/298

(56) References Cited

U.S. PATENT DOCUMENTS

| | | | |
|---|---|---|---|
| 4,674,883 A | | 6/1987 | Baurschmidt |
| 5,118,183 A | * | 6/1992 | Cargill et al. ............... 356/73 |
| 5,233,386 A | | 8/1993 | Terashita |
| 5,402,361 A | * | 3/1995 | Peterson et al. ........... 364/525 |
| 5,519,210 A | | 5/1996 | Berner |
| 5,929,413 A | * | 7/1999 | Gardner ..................... 235/379 |
| 5,945,341 A | * | 8/1999 | Howard, III ................ 436/46 |
| 6,141,120 A | * | 10/2000 | Falk ........................... 358/504 |
| 6,151,422 A | * | 11/2000 | Hayduchok et al. ........ 382/286 |
| 6,301,104 B1 | * | 10/2001 | Hu ............................. 361/684 |
| 6,327,047 B1 | * | 12/2001 | Motamed .................... 358/1.15 |
| 6,338,030 B1 | * | 1/2002 | Senn et al. .................. 702/189 |

FOREIGN PATENT DOCUMENTS

| | | |
|---|---|---|
| EP | 0 228 347 | 7/1987 |
| EP | 0 357 986 | 3/1990 |
| EP | 0 509 520 | 4/1992 |
| EP | 0 628 874 | 12/1994 |
| EP | 0 837 320 | 4/1998 |
| EP | 0 878 704 | 11/1998 |

* cited by examiner

Primary Examiner—Michael G. Lee
Assistant Examiner—Daniel A. Hess
(74) Attorney, Agent, or Firm—McCarter & English, LLP (57) ABSTRACT

A device (strip reader) for an automatic photoelectric measurement of measuring fields contained on a sheet or strip-shaped, opaque or transparent original comprising a housing, transport members for automatically pulling the original into the housing and for transporting the original along a transport path, and a spectrophotometric measurement arrangement as well as a controller in co-operation with the transport members and the measurement arrangement. The measurement arrangement is adjustable in a direction transverse to the transport direction and illuminates the measuring fields provided on the original with light of a defined quality, and receives the light remitted or transmitted from the measuring fields in dependence upon the original and converts this measuring light into electrical signals representing the spectra of the measuring fields. The controller controls the insertion and the transport of the original and converts the electrical signals generated by the measurement arrangement into digital measuring data. The measuring data are provided to an external computer via communication interfaces, preferably via the Internet or via e-mail, for further processing.

27 Claims, 4 Drawing Sheets

APPARATUS FOR AUTOMATIC MEASUREMENT OF MEASURING FIELDS

FIELD OF THE INVENTION

The invention relates to a device for automatic measurement of measuring fields.

BACKGROUND OF THE INVENTION

The invention relates to a device for an automatic photoelectric measurement of measuring fields being provided on a sheet or strip type, opaque or transparent original. Such devices which are commonly named automatic strip readers are used, for example, in the photographic industry for a routine control of wet chemical device components on one hand and for the control of the settings of a photographic copy device (printer) on the other hand.

For the control of wet chemical device components, film or paper developing baths, respective film chemistry or paper chemistry strips are measured. These strips already underwent a standardized exposure at the respective film or copy paper manufacturer, and they contain a different arrangement of various measuring fields which differ from manufacturer to manufacturer. The operator of the wet chemical units develops the strips in more or less regular intervals in the respective film or paper developing units. The developed film or paper strips are photometrically analyzed using a hand densitometer or the mentioned automatic strip reader, whereby the determined measurement data are compared to the target data of the manufacturer. Depending on the determined comparative results, the developing baths are refreshed or filled up, renewed, or maintained unchanged. To control the settings of a photographic printer, one or several standard negatives are projected onto the photographic paper which is developed using a standardized and tested chemistry. The developed pictures are again photometrically analyzed and the determined measurement data are compared to the target data of the manufacturer. In dependence upon the determined comparative values, the settings of the printer can be corrected or maintained. Further details for this and examples for typical measurement strips are found in U.S. Pat. No. 5,402,361 and U.S. Pat. No. 5,118,183, the disclosures of which are hereby incorporated by reference in their entirety.

A strip reader of this kind is described in U.S. Pat. No. 5,519,210, the disclosure of which is hereby incorporated by reference in their entirety. It includes a housing having an insertion slit arranged on its front side for a test strip—film or paper to be measured. A transport system is disposed within the housing in order to draw the supplied test strip in through the insertion slit and to advance it along a transport path and in doing so to guide it in a defined manner. In the vicinity of the transport path, a densitometric measurement arrangement is provided which can be operated in both, transmission and remission mode, so that transparent (film) and opaque (paper) test strips can be equally measured. While the test strip is inserted, the measurement arrangement photoelectrically scans subsequent measuring fields in the direction of the transport path and transfers the electrical signals thus obtained to a controller which calculates digital measuring data therefrom which represent the (color) density of the scanned measuring fields on the test strip. In addition, the densitometric measurement arrangement is adjustable transverse to the transport direction of the test strip to allow the measuring of test strips having a two-dimensional array of measuring fields, so that the scanning can be carried out sequentially manner in several parallel tracks. The motion and function sequences are carried out under the control of the digital controller. Furthermore, a bi-directional interface connected to the controller is provided through which a data exchange with an external computer can occur, whereby the generated digital measuring data of the individual measuring fields of the test strip can be transferred to the external computer. In the case that the device is to be operated autonomously, it is additionally provided with a suitable keyboard and an optical display unit, which is connected to the controller and operates in concert with the same. After the measuring fields are measured, the test strip is ejected again through the insertion slit.

A further known strip reader is subject of U.S. Pat. No. 5,402,361 and U.S. Pat. No. 5,118,183, the disclosures of which are hereby incorporated by reference in their entirety. These devices are also equipped with densitometric measuring arrangements for the photoelectric measurement of the measuring fields contained on the control strip, but the densitometric measuring arrangements are not laterally adjustable so that the scanning of test strips with a two-dimensional measuring field arrangement is comparatively laborious and only possible by multiply inserting the test strip from the side in an off-set manner. The strip readers presented in these documents are connected to a telephone network by means of a suitable data interface and a modem, and furthermore are connected to a remote computer, for example a central quality control station. The remote computer can retrieve digital measuring data from the strip reader or, for example, can send control commands and messages to the strip reader, whereby the control commands trigger certain functions, and messages can be displayed, for example, on the display of the strip reader.

The densitometric analysis of the test strips which has been exclusively used to date in known strip readers is not sufficient in view of increased demands for quality in modern photographic production lines and color management. It is an object of the present invention to improve a device of the generic type in so far as to allow for a more accurate and dependable analysis of the measuring fields of the test strips, so that better justice can be done to the demands and possibilities of modern photographic high quality production lines and that the device can also be particularly used for color management.

SUMMARY OF THE INVENTION

The spectral measurement in accordance with the invention of the measuring fields allows a more accurate and objective evaluation of the same, which in turn allows a more accurate and better adjustment of the individual parts of the photographic production line. The device is particularly suited for use in so-called color management, where measuring strips with very many measuring fields (far above 100) are used and colorimetrically measured with high precision.

In order to also measure very dense transparent originals, an additional densitometric measuring arrangement is provided in accordance with a preferred embodiment. This additional measuring arrangement makes the device more universally applicable.

In accordance with a further advantageous embodiment, the spectral measuring arrangement or the spectral and densitometric measuring arrangements are adjustable laterally to the direction in which the original moves. As a result, an automatic measurement of originals having two-dimensional measuring field arrangements is possible.

Further particularly advantageous embodiments and improvements of the device in accordance with the invention are the subject of the dependent claims.

BRIEF DESCRIPTION OF THE DRAWINGS

The above objects and features of the present invention will be more apparent from the following description of the preferred embodiments with reference to the accompanying drawings, wherein.

DETAILED DESCRIPTION OF THE INVENTION

Figure 1:
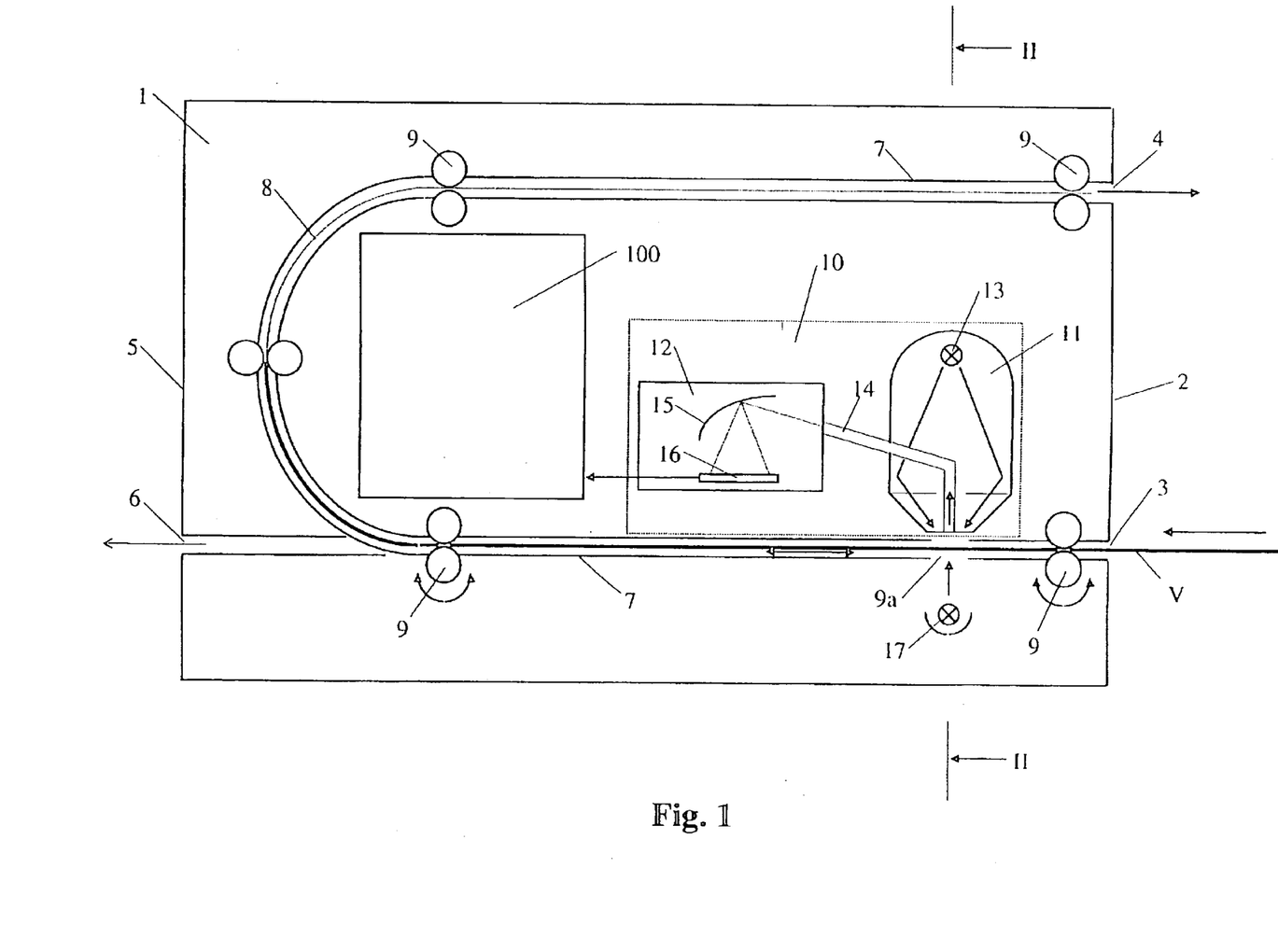
FIG. 1 shows a schematic longitudinal sectional view through the device in accordance with the invention.

As is apparent from FIG. 1, the device in accordance with the invention includes a housing 1 having a front side 2 on which an insertion opening in form of an insertion slit 3 is disposed. Above the insertion slit 3 there is a first exit opening in form of an exit slit 4. A second, also slit-shaped exit opening 6 is provided on the rear 5 of the housing 1. Between the insertion slit 3 and the first exit slit 4 is a guide channel 7 in form of a lying U which forms a transport path 8 for the original V to be measured, said original V being inserted into the housing 1 through the insertion slit 3. Motorically driven transport roller pairs 9 are arranged along the guide channel 7 or the transport path 8, wherein the original V is being drawn inside using the motor driven transport roller pairs 9 and is moved along the transport path in both directions. The transport roller pairs 9 are controlled by a controller 100.

The original V to be measured is manually inserted into the housing 1 through the insertion slit 3 and ejected through the first exit slit 4 by means of the transport roller pairs 9 after the measuring is completed. Alternatively, the original can also be ejected through the insertion slit 3, and in this case, the first exit slit 4 is not necessary anymore. In the case that there is sufficient space behind the housing 1 in practical applications, the original can also be ejected through the rear exit slit 6. For this reason, the housing 1 is provided with manually adjustable switching members of any type, not shown, which guide the original V either along the bent transport path 8 to the front exit slit 4 or directly to the rear exit slit 6. Naturally other types of guiding members defining the transport path 8 can be provided in place of the presented guide channel 7, for example. Furthermore, suitable guiding members are also provided at the side (in FIG. 1 acting in the direction perpendicular to the plane of the drawing) as in known strip readers, which are however not presented for reasons of clarity. The guiding members at the side are designed preferably for originals of varying width, for example as the described stepwise guiding ramps in U.S. Pat. No. 5,519,210.

FIG. 1 presents four transport roller pairs 9. It is apparent that for practical purposes, more or less transport roller pairs can be provided. In one embodiment, the device is only equipped with one transport roller pair which is disposed immediately behind the scanning window 9a of the guiding channel 7. In this way, originals V which are too short to be ejected from one of the two ejection slits 4 or 6, are ejected again from the front through insertion slit 3.

Besides the U-shaped bend of the transport path 8, the device corresponds substantially to the device described in U.S. Pat. No. 5,519,210 with respect to the guidance and the insertion or drive of the original to be measured, so that the person of skill in the art does not need a further detailed description in this regard.

The already mentioned scanning window 9a (in the presented embodiment) is provided in the direction of insertion of the original V just behind the first transport roller pair 9 in the guiding channel 7 (or in or between the other guiding members). The scanning window 9a extends transversally to the direction in which the original V is advanced (perpendicular to the plane of the drawing).

A spectral measuring arrangement 10 above the guiding channel 7 substantially consists of a detector 11 and a converter 12. The detector 11 includes a light source 13 of a known kind and various optical members (not presented), in order to guide the light coming from the light source 13 in a circular manner and at a standardized angle of incidence of about 45° onto the measuring fields of the original V which is guided through beneath the detector. Furthermore, the detector includes further optical members in order to receive measuring light (remitted or transmitted) at an angle of about 90° coming from a measuring field of the original V and to direct it to the converter 12. The latter mentioned optical members are symbolized in the drawing by a light guide 14. A particularly suitable detector of this kind is described, for example, in U.S. Pat. No. 4,929,084, the disclosure of which is hereby incorporated by reference in its entirety.

The converter 12 is designed as a diode array spectrometer of a known kind and substantially includes a concave reflexion diffraction grating 15 and a linear field 16 of photosensitive diodes. The diffraction grating 15 locally splits the measuring light which it receives from the detector 11 via the light guide 14 in a wavelength-dependent manner. The photo diode array 16 converts the spectrally split measuring light into respective electrical signals, so that the spectral components of the measuring light given off the scanned measuring field of the original are available in electronic form.

Spectral measurement arrangements of this and similar construction are common in modern spectrophotometers and are described, for example, in detail in U.S. Pat. No. 5,040,889, U.S. Pat. No. 4,929,084, and EP-B-0 489 286, the disclosures of which are hereby incorporated by reference in its entirety, so that no further explanation is necessary for the person skilled in the art.

In accordance with an advantageous aspect of the invention, an additional light source 17 is provided below the detector 11 on its optical axis so that the spectral measurement arrangement 10 can also measure transparent originals, wherein the light source 17 illuminates the original or the measuring fields contained thereon from below. The measuring light transmitted from the transparent original V is in turn captured again by detector 11 and supplied to the converter 12. It is apparent, that in the case of transparent originals V, the light source 13 in detector 11 is not activated.

Furthermore, controller 100 as already mentioned and realized through a digital computer system is provided in housing 1 for the control of all motion and function sequences of the device. Controller 100 is connected in particular with the converter 12 or the photo diode array 16 contained therein, whereby it processes the generated electrical signals into corresponding digital measuring data, as is known from digital spectrophotometers (compare for example U.S. Pat. No. 5,040,889). The interaction of the controller 100 with the remaining components of the device is explained further down below with respect to FIG. 4.

Figure 2:
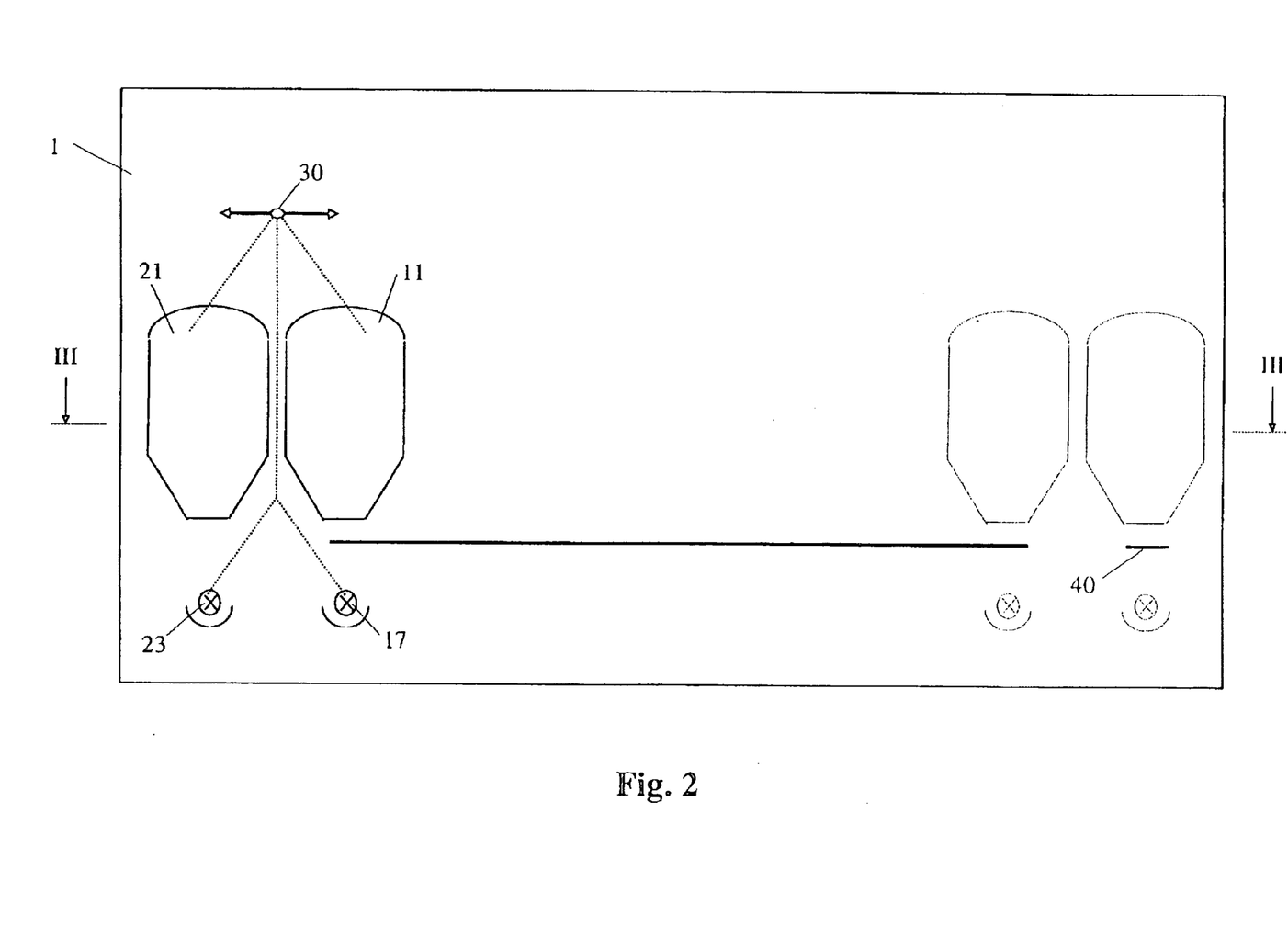
FIG. 2 shows a strongly simplified schematic cross-sectional view which extends substantially along line II—II in FIG. 1.
Figure 3:
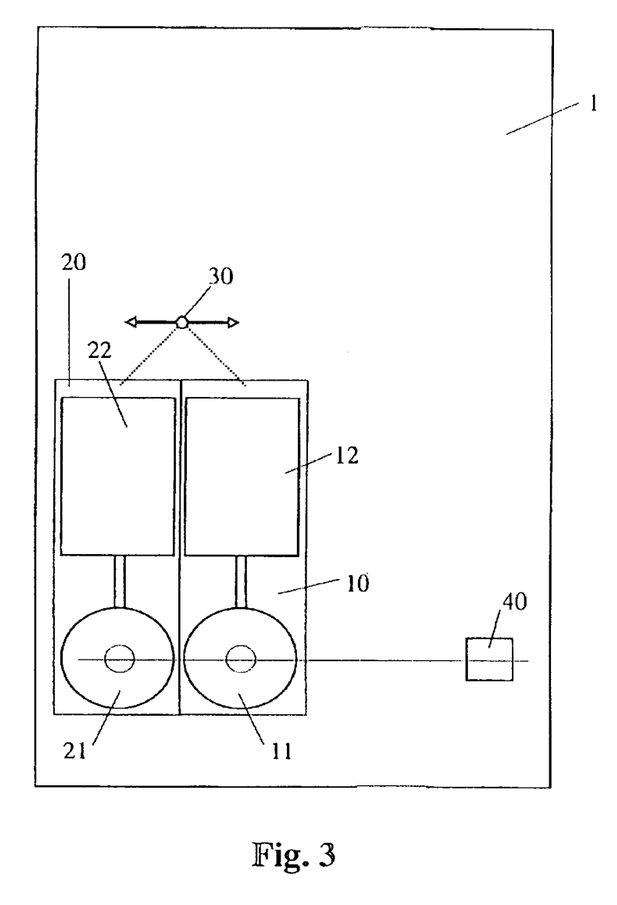
FIG. 3 also shows a strongly simplified view of line III—III of FIG. 2.

Transparent originals (film strips) are often optically dense, so that there is not sufficient light available for a spectrophotometric evaluation. In accordance with a further important aspect of the present invention, a densitometric measurement arrangement 20 is provided in addition to the spectral measurement arrangement 10 for allowing the measurement of such dense originals. The densitometric measurement arrangement 20 is placed, for example, directly adjacent to the spectral measurement arrangement 10, as is shown in FIGS. 2 and 3.

The densitometric measurement arrangement 20 is conventionally constructed, for example as is described in detail in U.S. Pat. No. 5,519,210. It comprises a similar detector 21 as in the spectral measurement arrangement 10 and a converter 22 optically connected thereto. The converter 22 generates electrical signals by means of densitometric filters and photoelectric converters, wherein the electrical signals correspond to the intensities or densities of the measuring light originating from the original in the three classic spectral ranges red, blue, and green. The converter 22 can also be arranged directly below the detector 21. A light source 23 for illuminating the original from below is arranged below the detector 21 for the densitometric transmission measurement, similar as in the spectral measurement arrangement 10. If the densitometric measurement arrangement 20 is only used for through-light measurements, the light source in the detector is of course obviated. Like the spectral measurement arrangement 10, the densitometric measurement arrangement 20 is connected to the controller 100, whereby the latter processes the generated electrical signals in a known manner into corresponding digital measuring data which represent the densitometric color densities of the scanned measuring fields on the original.

Film and paper chemistry strips and especially the measuring strips that are used in color management, often have a two-dimensional arrangement of measuring fields. In order to be able to also automatically measure such originals without elaborate manipulations, both measurement arrangements 10 and 20 are motorically adjustable transverse to the direction of transport of the original V (in FIG. 1 thus perpendicular to the plane of the drawing), in accordance with a further important aspect of the invention. This adjustability or the adjustment members required therefore are symbolized by a double arrow 30 in FIGS. 2 and 3. Naturally, the light sources 17 and 23 are thereby also adjustable together with the measurement arrangements, so that the relative positions of the light sources to their respective detectors remain the same.

The adjustment of the measurement arrangements 10 and 20 and the associated light sources 17 and 23 is realized by two motor drives 31 and 32 (FIG. 4) under control of the controller 100. Naturally, four independent drives can be provided or a single common drive in combination with a respective kinematic coupling of the components to be moved.

In accordance with a further important aspect of the invention, the device is equipped with an integrated white reference field 40, which is arranged in the plane of the original in the vicinity of the right end of (the moving track shown in FIGS. 2 and 3 of the measurement arrangements 10 and 20. This white reference field 40 is sought out and measured by the spectral measurement arrangement 10 in certain time intervals or, for example, after each measurement of an original. Using the (spectral) digital measuring data thus obtained, the controller 100 can then in a known manner, as described for example in EP-A-0 878 704, the disclosure of which is hereby incorporated by reference in its entirety, perform an automatic white calibration. If necessary, the white reference field 40 can also be used for the calibration of the densitometric measurement arrangement. Instead of the single white reference field 40, it is also possible to use several reference fields of different color or grey shades for the calibration, as is also described more closely in EP-A-0 878 704.

Figure 4:
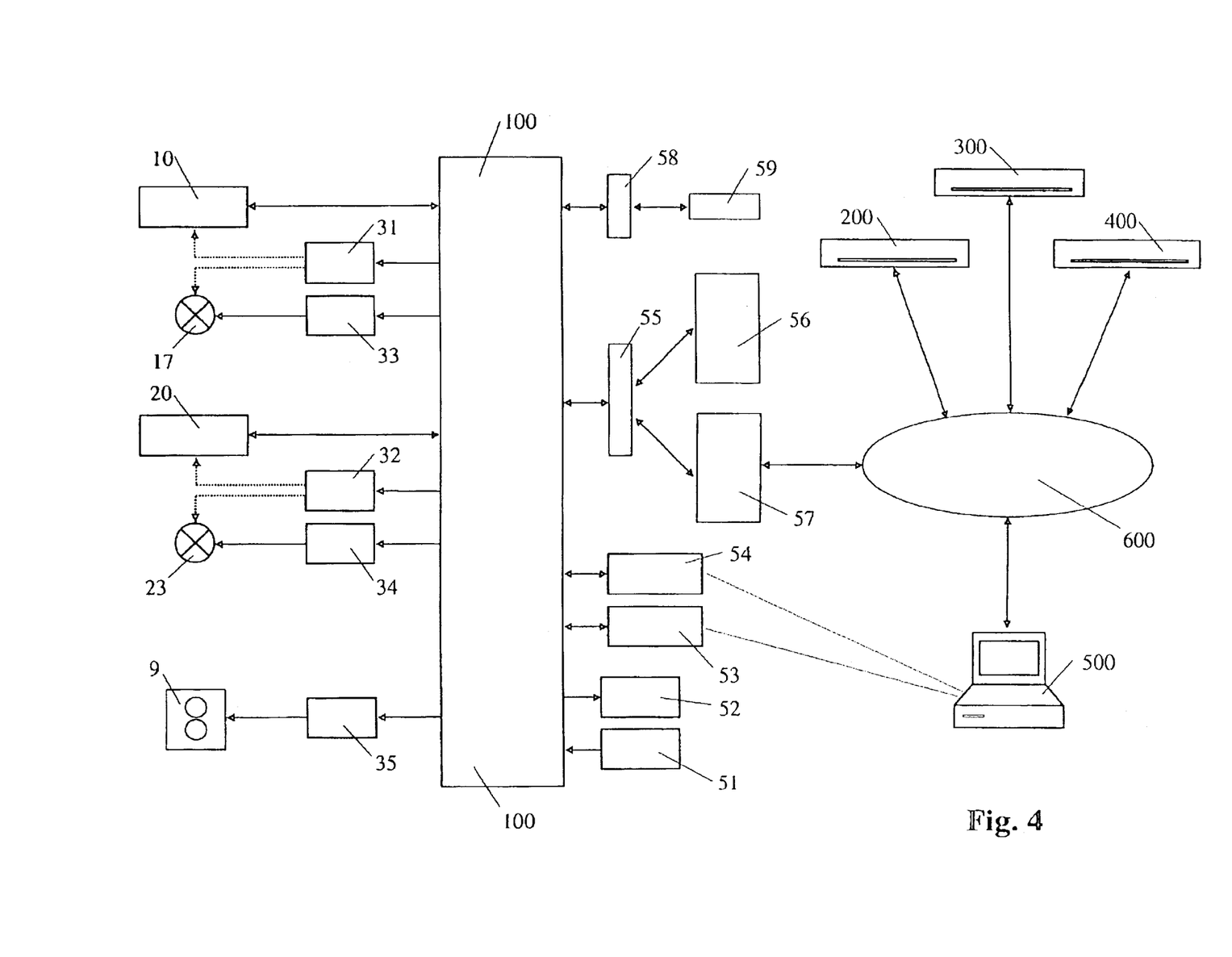
FIG. 4 shows a block scheme of the most important components of the device and their integration into a network.

FIG. 4 is a block diagram showing the connection of the already mentioned components of the device with the controller 100 as well as various further components. The spectral measurement arrangement 10 and the densitometric measurement arrangement 20 are directly connected to the controller 100, whereby the necessary analog signal amplifiers which are commonly contained within converter components, are not presented. The analog/digital conversion occurs in the controller 100. The two light sources 17 and 23 are controlled by the controller 100 by way of respective lamp drivers 33 and 34. The motor drives 31 and 32 are also controlled by the controller 100 (by not shown driver stages). The transport roller pairs 9 for the advance of the original to be measured, which are kinematically coupled to each other by, for example, means of a driving belt, are driven by a motor 35 which is controlled by the controller 100 by way of a not shown driver stage.

Further, the device can include a keyboard 51 and an optical display unit 52, which act in combination with the controller 100 in a known manner. The keyboard and the display unit, for example, can be omitted in the case of a device designed as a built-in unit.

Furthermore, the device is provided with a serial bi-directional data interface 53 and/or a USB interface 54, which are connected to controller 100 for allowing the communication of the device or its controller 100 with an external computer 500, for example, in a known manner. Digital measuring data can be transferred to the external computer via these interfaces in a known manner (for example, as described in U.S. Pat. No. 5,402,361). Furthermore, the device can also be controlled by the external computer via these interfaces. The programming required therefore is known from modern digital spectrophotometers and hence does not require a detailed explanation.

Further, the device comprises an extension connection 55 for a network interface 56 or a modem 57 as well as a connection 58 for a bar code reader 59. The bar code reader allows, if necessary, the reading of data (FIG. 5) provided on the original V in the form of a bar code BC to the controller 100.

Preferably, the network interface 56 and the modem 57 are designed as optional modules, which can be selectively connected to the device. Naturally, the network interface 56 and/or the modem 57 can also be permanently built-in to the device.

The network interface 56 (e.g., Ethernet) allows the connection of the device to a data network and thus the connection to an external computer, for example. By means of the modem 57 it is possible to make a connection to the external computer 500 via the public telephone network either directly or via the Internet 600 and vice versa. It is a prerequisite, of course, that the external computer 500 is also equipped with corresponding communication interfaces. The external computer 500 can, for example, belong to a central quality control location, where the digital measuring data that are generated with the device in accordance with the invention are analyzed. In doing so, it is possible, of course, to connect further devices 200, 300, 400 in accordance with the invention to the computer 500, via the Internet 600 (or the telephone net). It is apparent that access to the Internet, if necessary, is also possible via the network interface 56, when the network has an Internet-connection. The required software (programming of the controller 100) for the data communication via a data network and the Internet is known to a person of skill in the art and hence does not require a detailed explanation.

The respective functional sequences for the actual measurement of the original are substantially equal to the device known from U.S. Pat. No. 5,519,210 for example.

The controller 100 stores the measuring field arrangements on the original for the most common types of originals in a suitable manner in assigning a notation or a code for the respective type of original. The data describing the measuring field arrangements are denoted in the following as (original) configuration data.

Before a measurement of the original can be performed, it is necessary to choose and adjust the respective type of original, for example, using the keyboard 51. In accordance with a particularly advantageous embodiment of the device in accordance with the invention, this selection can also be automatically performed by scanning the code of the type of the original which is contained on the original. This variant is explained in more detail further down below. Furthermore, the controller must be informed, for example, by way of the keyboard 51, whether the original is an opaque or transparent original. Alternatively, this can be automatically determined by means of sensors known in the art. Finally, it needs to be determined and adjusted whether the measurement is to be performed spectrally or densitometrically. In accordance with the invention, this adjustment can also be performed automatically using controller 100 by measuring at least one measuring field and using the determined measuring data, for example, in connection with a density criterion.

For the measurement, the original V is inserted into the insertion slit 3 until it is taken over by the first transport roller pair 9 and then transported further by automatic control. If needed, the mentioned measurements for the identification of the type of original, the differentiation between opaque and transparent, and the determination between spectral or densitometric measurement are carried out first, and the controller 100 is prepared accordingly. Alternatively, these prepared settings can be entered manually using keyboard 51, such as in U.S. Pat. No. 5,519,210 for example.

Depending on the type of original and its configuration data, the controller 100 first transversely moves the appropriate measurement arrangement 10 or 20 into a position, wherein the detector 11 or 21 (and the light source 17 or 23) is located above the first measuring field column. Now, the original is transported further inward until all measuring fields of the first column are measured. Subsequently, the measurement arrangement is moved to the next measuring field column using the configuration data of the original and the original is transported in a reverse direction until this column is also completely measured. This procedure is continued until all measuring fields of the original are measured. The digital measuring data thus obtained are temporarily stored in the controller 100 for further (internal or external) processing. Subsequently, the original is ejected again through one of the exit slits 4 or 6, or also through the insertion slit 3, as described above. The obtained digital measuring data can be displayed in a suitable manner on the optical display unit 52. However, it is preferred that the data are transferred to the external computer via one of the communication interfaces, where the actual analysis of the data takes place. This is described in more detail further down below.

Figure 5:
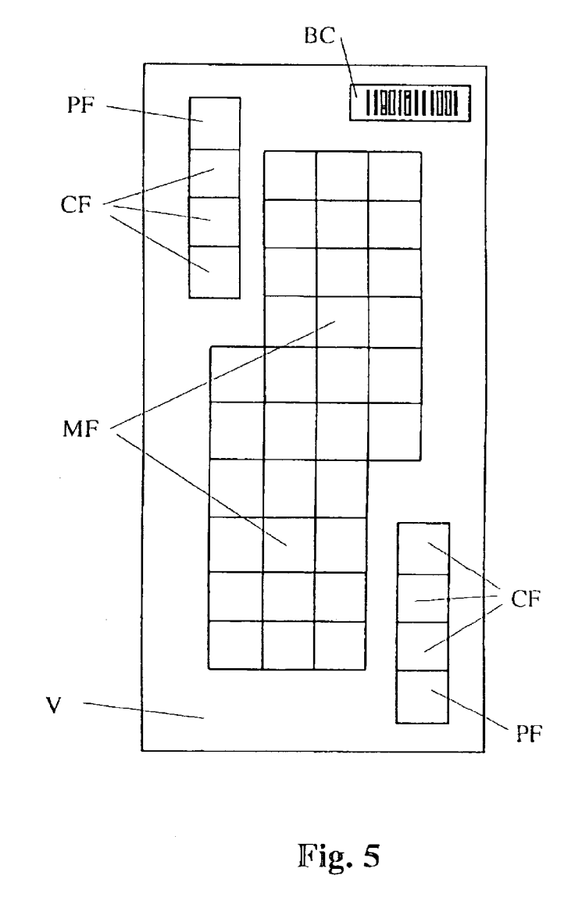
FIG. 5 shows an exemplary original having measuring fields disposed thereon.

FIG. 5 shows an exemplary original V which has some exceptional features in comparison to common film and paper test strips and for which separate protection is sought.

The original V has a two-dimensional arrangement of measuring fields MF in the central region, which are adapted to the intended use of the original. Examples for typical measuring fields are shown in the already above-mentioned documents U.S. Pat. No. 5,118,183 and U.S. Pat. No. 5,402,361. The type of measuring fields and their arrangement on the original are characteristic for the respective type of original.

In each one of two diametrically opposed corners (in the example shown), there are four special measuring fields aligned one behind another in the longitudinal direction of the original V, wherein the field closest to the corner is a positioning field PF and the three other fields each represent a code field CF. The color of the fields is used as a coding information, wherein this is preferably limited to the primary colours red, blue, and green.

The positioning fields PF have different colours. Once the original is inserted into the device, the positioning field is the first field to be measured and its colour is determined in the controller using the measuring data. By using the colour, the controller 100 can then determine whether the original V was inserted into the device with its front edge (at the top in the drawing) or with its rear edge (at the bottom in the drawing).

The three remaining code fields CF through the combination of their colours respectively form a code for the type of the original. By limiting each code field to three colours, it is possible to distinguish between 27 different types of originals using three code fields CF. If it is desired to have more original types, it is necessary to provide a respectively higher number of code fields CF or to allow more colours per field (preferably also visually reliably distinguishable).

The different codes for the type of originals are stored in the controller 100, as already mentioned, in relation to respective configuration data, which represent the arrangement of the measuring fields MF on the original. Naturally, the (predetermined) positions of the positioning fields PF and the code fields CF are also stored in the controller. When the original V is inserted into the device, the spectral measurement arrangement 10 (or alternatively also the densitometric measurement arrangement 20) is first laterally moved into such a position that the positioning field and the code fields can be scanned. Using the measuring data thus obtained, the colours of these scanned fields are determined and thus the positioning code and the code for the type of original. Using the code for the type of original, the configuration data (arrangement of the measuring fields MF) belonging to the respective type of original are chosen or retrieved from memory, whereby the insertion direction (front or rear edge) determined from the positioning code is taken into consideration accordingly. The controller knows the positions of the measuring fields MF to be measured on the original V, so that the measuring fields MF can be sequentially selected and measured.

The advantage of coding the type of original directly on the original is, that it is not necessary to provide the information regarding the type of original to the device (e.g. via the keyboard) so that the handling is simplified and entry errors are avoided. The positioning code also simplifies the handling since it is no longer necessary to pay attention that the original is inserted into the device in the correct orientation.

If the device is utilized for measuring originals employed in different production lines, then the measurement results must be assigned to the respectively correct production line. This can be done, for example, by manually entering a corresponding original identification code which is then assigned in the controller 100 to the measuring data of the respective original in form of original identification data. In accordance with a further important aspect of the invention, this original identification code can also be directly provided on the original itself and can be automatically read in from the original.

In the case of pre-exposed originals for the testing of chemical treatment baths, the code is preferably provided on the original in the form of a bar code BC. The bar code can thereby be printed, for example, on a label that is glued to the original in a suitable location. This original identification code can be read in by the controller using the bar code reader 59.

Originals that are exposed within a printer for testing the same have the original identification code exposed preferably directly onto the original in the printer. Naturally, the printer must be capable of doing this, which is the case in modern digital printers. The exposed code can be formed of a number of coloured code fields CF, similarly to the code for the type of original, and can be located on the original, for example in line with the code for the type of original. The original identification code is read by the controller 100 in the same manner as the code for the original type upon insertion of the original V into the device, whereby the controller 100 forms corresponding original identification data using the original identification code and subsequently assigns the determined digital measuring data to the measured original.

In the prior art devices described in the above cited documents U.S. Pat. No. 5,519,210 and U.S. Pat. No. 5,118,183, the digital measuring data of the measured originals are transferred to an external computer, wherein this computer can also be provided in a remote location and is then connected to the device via the telephone network. The transfer of the data is either initiated by the device or by the external computer. This process has the disadvantage that a permanent connection for communication must exist between the device and the external computer.

In accordance with a further important aspect of the invention the device is designed to access the Internet and to store the digital measuring data on the Internet. This can be done for example using the known FTP (File Transfer Protocol), but is preferably carried out via e-mail. In doing so, the measuring data are processed together with the original identification data to yield a data file of an internationally standardized format IT8 and this data file is then sent to an e-mail address as an attachment to an e-mail message for this purpose. The data can then be retrieved therefrom through the external computer at any given time. Alternatively, the external computer can also deposit an e-mail destined for the device on the Internet, and the device can retrieve this e-mail at a certain point in time from the Internet. In this manner it is possible to send from the external computer to the device messages which can be optically displayed on the display unit of the device. Furthermore, it is also possible to transfer control and configuration data for the device into the device. The software required for the e-mail communication which is stored and run in the controller is standard nowadays and a person of skill in the art does not require an explanation therefor.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A device for the automatic photoelectric measurement of measuring fields contained on an original, the device comprising:

a housing having an insertion opening for insertion of the original, said original having a front edge and a rear edge;

a transport structure for automatically pulling the original into the housing and for transporting the original along a transport path;

a detector of a photoelectric measurement arrangement for providing light of a defined quality to measuring fields contained on the original, for receiving measurement light being remitted or transmitted from the measuring fields pending on the original, and for converting the measurement light into electrical signals representing the colour characteristics of the measuring fields, said photoelectric measurement arrangement being a spectral measurement arrangement, for generating electrical signals representing the spectra of the measured measuring fields on the original; and a controller for cooperating with the transport structure and the spectral measurement arrangement for controlling the pulling in and transport of the original, for converting the electrical signals generated by the spectral measurement arrangement into digital measuring data, and for supplying said digital measuring data to an interface for access by an external computer and further processing;

wherein configuration data representing the arrangement of the measuring fields on the original for a plurality of different types of originals is stored in the controller; said controller being designed for determining from generated digital measuring data of pre-defined code fields an original identification code specific for the type of original and defined by colours of the pre-defined code fields, for selecting stored configuration data based on the determined original identification code for the type of original that contains said identification code, and for controlling the measurement of individual measuring fields on the original based on the selected configuration data, wherein the controller determines whether the front edge or the rear edge of the original first enters the insertion opening of the housing, and wherein the controller is designed for determining a positioning code on the original, said positioning code being formed through colours of pre-defined positioning fields, said controller determining the positioning code from digital measuring data generated from said positioning fields, and controlling the measurement of the individual measuring fields of the original using the positioning code.

2. The device of claim 1 comprising:
An adjustment structure controlled by the controller, the adjustment structure adjusting the spectral measurement arrangement transversely to the transport path of the original, such that measuring fields of an original having a two-dimensional measuring field arrangement can be measured.

3. The device of claim 1, wherein an adjustment structure adjusts the densitometric measurement arrangement transversely to the transport path of the original.

4. The device of claim 2, wherein the spectral measurement arrangement performs transmission measurements and includes a light source for shining light through a transparent original, said light source being transversely adjustable together with the spectral measurement arrangement.

5. The device of claim 2 wherein the densitometric measurement arrangement performs transmission measurements and includes a light source for shining light through a transparent original, said light source being transversely adjustable together with the densitometric measurement arrangement.

6. The device of claim 2 comprising:
a white reference field, wherein the adjustment structure positions the spectral measurement arrangement near the white reference field under the control of the controller, the spectral measurement arrangement spectrally measuring the white reference field, said controller performing an automatic white-calibration based on the spectral measuring data of the white reference field.

7. The device of claim 1, wherein the controller determines an original identification code from digital measuring data generated by code fields, said original identification code being formed through colours of defined code fields, said controller forming corresponding digital original identification data from the original identification code and assigning said original identification data to digital measuring data of the respective original.

8. The device of claim 1, comprising:
a bar code reader which is connectable to the controller and interacts with the controller, said bar code reader reading an original identification code in the form of a bar code into the controller, said controller assigning the retrieved original identification code or original identification data derived therefrom to digital measuring data of the respective original.

9. The device of claim 1, wherein the transport path inside the housing is substantially U-shaped such that the original is redirected by substantially 180°.

10. The device of claim 9, wherein the transport path extends from the insertion opening to a first exit opening, said first exit opening being disposed on a same side of the housing as the insertion opening.

11. The device of claim 10, wherein a second exit opening is provided on a side of the housing opposite to the insertion opening, and wherein the transport path is adjustable such that said transport path extends from the insertion opening to one of the first exit opening and the second exit opening.

12. The device of claim 1 comprising:
a serial interface for a bi-directional communication with the external computer, said serial interface being in cooperation with the controller, for transfer of digital measuring data to the external computer and for control of the function and configuration of the device by means of the external computer.

13. The device of claim 1, comprising:
a USB interface for a bi-directional communication with the external computer, said USB interface being in cooperation with the controller, for transfer of digital measuring data to the external computer and for control of the function and configuration of the device by means of the external computer.

14. The device of claim 1, comprising:
a network interface for a bi-directional communication with the external computer via a data network, said network interface being in cooperation with the controller, for transfer of digital measuring data to the external computer and for control of the function and configuration of the device by means of the external computer.

15. The device of claim 14, comprising:
an extension connection for providing a modular connection between the network interface and the controller.

16. The device of claim 1, comprising:
a modem for a bi-directional communication with the external computer via a telephone network and/or the Internet, said modem being in cooperation with the controller, for transfer of digital measuring data to the external computer and for control of the function and configuration of the device by means of the external computer.

17. The device of claim 16, comprising:
an extension connection for providing a modular connection between the modem and the controller.

18. The device of claim 1, wherein the controller comprises an e-mail software for, via the interface, sending an e-mail message to the Internet and receiving an e-mail message from the Internet, and wherein the communication with the external computer is carried out via e-mail.

19. The device of claim 18, wherein the controller is operable for sending digital measuring data, and configuration and control data, as an e-mail attachment to the external computer, and for receiving digital measuring data, and configuration and control data, as an e-mail attachment from the external computer.

20. The device of claim 19, wherein the controller provides the digital measuring data in IT8 format.

21. The device of claim 19, wherein the controller provides the digital measuring data in an IT8 format and wherein the controller sends the digital measuring data as an e-mail attachment in the IT8 format.

22. The device as defined in claim 1, further including an additional densitometric measurement arrangement, cooperating with the controller for generating electrical signals representing the colour densities of the measured measuring fields at least for the colours red, blue and green.

23. A test original for testing the settings of a photographic production unit, the test original comprising:
a plurality of measuring fields in dependence upon a respective use, wherein the plurality of measuring fields includes a machine-readable code, said code containing information about the type of the original and information about the production unit in which the original is used;
a code for differentiating a front edge from a rear edge of said test original; and
a positioning code being formed through colours of pre-defined positioning fields, wherein the positioning code is used for controlling the measurement of the individual measuring fields of the original.

24. The test original of claim 23, comprising:

a code for automatically determining an orientation of the original during an insertion process into a measuring device suitable for measuring the measuring fields.

25. The test original of claim 23, comprising:

a bar code containing information about the production unit in which the original is used.

26. The test original of claim 23, wherein the code is formed of one or more coloured code fields.

27. A device for photoelectric measurement of measuring fields, the device comprising:

a housing having an insertion opening for insertion of an original, said original having a front edge, a rear edge and containing measuring fields;

a transport structure for transporting the original along a transport path within the housing;

a detector of a photoelectric measurement arrangement for providing light of a defined quality to the measuring fields on the original, for receiving measurement light being remitted or transmitted from the measuring fields on the original, and for converting the measurement light into electrical signals representing the colour characteristics of the measuring fields; and a controller for cooperating with the transport structure and the spectral measurement arrangement for controlling transport of the original, for converting the electrical signals generated by the photoelectric measurement arrangement into digital measuring data, and for supplying said digital measuring data to an interface for access by a processor;

wherein configuration data is accessible by the controller, said configuration data permitting the controller to determine the type of original based on the arrangement of measuring fields on the original, wherein the controller determines an identification code from generated digital measuring data of a pre-defined code field on the original, selects configuration data based on the said identification code, and controls measurement of individual measuring fields on the original based on the selected configuration data, wherein the controller determines whether the front edge or the rear edge of the original first enters the insertion opening of the housing, and wherein the controller is designed for determining a positioning code on the original, said positioning code being formed through colours of pre-defined positioning fields, said controller determining the positioning code from digital measuring data generated from said positioning fields, and controlling the measurement of the individual measuring fields of the original using the positioning code.

* * * * *